United States Patent [19]

McSpadden

[11] Patent Number: 4,605,025

[45] Date of Patent: Aug. 12, 1986

[54] POWERED DENTAL FLOSSING DEVICE

[76] Inventor: John T. McSpadden, 2112 N. Roan St., Johnson City, Tenn. 37601

[21] Appl. No.: 610,041

[22] Filed: May 14, 1984

[51] Int. Cl.$^4$ ............................................. A61C 15/00
[52] U.S. Cl. .................................................. 132/92 R
[58] Field of Search ............. 132/91, 92 R, 93, 92 A; 433/141

[56] References Cited

U.S. PATENT DOCUMENTS 4,265,257  5/1981  Salyer ................................ 132/92 R
4,307,740  12/1981  Fioriudez et al. ................ 132/92 R Primary Examiner—Robert Peshock

[57] ABSTRACT

A dental flossing device having a unique and highly effective means for imparting oscillatory (term includes vibratory) motion to the floss only and precisely at such times as such motion is needed. The said means comprises a mechanical clutch which is intermediate the power element and the floss holder (stringer), wherein the clutch is responsive to force applied against the floss to engage the floss holder with the power element to begin oscillation of the floss.

10 Claims, 4 Drawing Figures

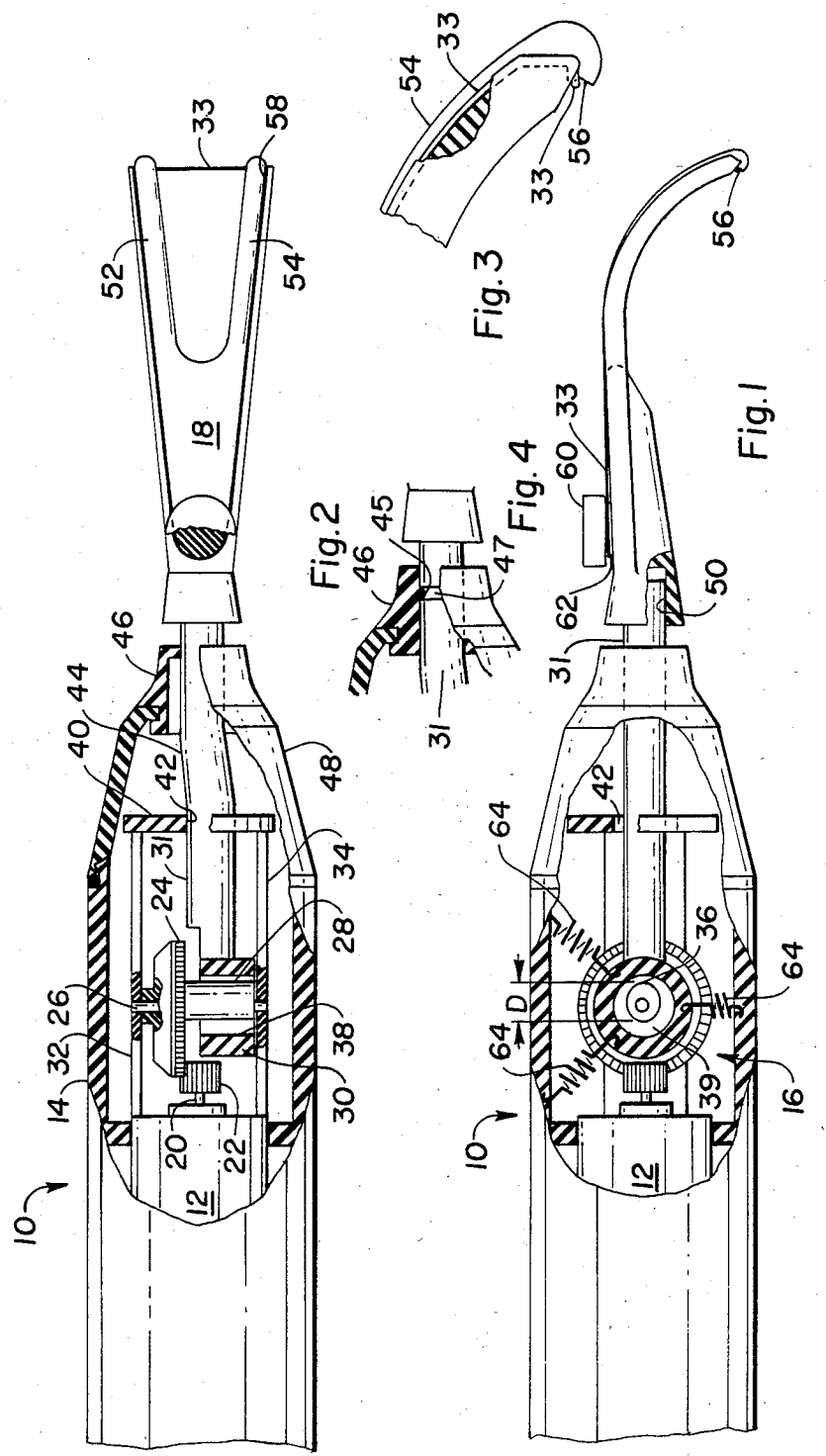

POWERED DENTAL FLOSSING DEVICE

This invention concerns a dental flossing device, and in particular concerns such a device having a unique and highly effective means for imparting oscillatory (term includes vibratory) motion to the floss only and precisely at such times as such motion is needed.

It is of course recognized that the accumulation of dental plaque is the principle etiologic factor of dental caries, gingivitis and other forms of periodontal disease. The known facts about deseases which affect the dentition and its supporting structures shown the need for interproximal cleansing of both tooth and gingival tissues. It is also well accepted that since the toothbrush alone cannot effectively remove interproximal plaque, dental floss should be incorporated in regular oral hygiene home-care procedures. Moreover, regular flossing can reduce interproximal surface dental caries and sulcular bleeding, improve gingival health, and may actually prevent the progression of periodontal disease in both children and adults.

The effectiveness of floss for interproximal cleansing has been well validated, however, proper flossing of teeth is not a simple procedure. Free-hand or even device-held flossing can be a complex task to learn and reliably perform, particularly in regard to insertion of the floss without its snapping at tight contact points. This task is further complicated by the need to reciprocate the floss to properly clean the interproximal and subgingival areas.

A marked improvement over free-hand flossing and simple mechanical floss holders have been made by powered flossing devices such as shown for example in U.S. Pat. Nos. 3,421,524; 3,534,745; and 4,338,957. In these powered devices, the floss which is typically mounted on and stretched between a pair of tines or prongs is set into its oscillatory motion upon actuation of an off-on switch located on the electrical motor housing or body of the device. A problem associated with such devices however, is that oscillatory and often harsh contact of sensitive tissue with the tines can occur in moving the floss into position for interproximal insertion. This problem is further aggravated by the constant motion of the floss during the attempted interproximal placement, which motion renders such placement difficult and increases greatly the aforesaid contact of the tines with the sensitive tissue.

The obvious solution to this problem is, of course, to shut off the electric motor during placement of the floss and to turn the motor back on when ready to floss. The disadvantages of such an approach are readily apparent, particularly in regard to the time wasted in performing the switching operations and in waiting each time for the oscillatory motion of the tines to cease as the motor and gearing mechanism wind down.

The present invention has as its principal objects therefore, to provide a powered dental flossing device which (1) minimizes the harsh, uncontrolled oscillatory contact of the floss tines with the soft tissues and other portions of the mouth and teeth, (2) which greatly facilitates placement of the floss for interproximal insertion, (3) which does not have to be turned off for proper floss placement, and (4) which provides a much safer and easier to handle flossing device than any heretofore known.

These and other objects hereinafter becoming evident have been attained in accordance with the present invention through certain discoveries disclosed and claimed herein, paramount of which is that if a clutch mechanism is built into the oscillation unit of the device the tines can be brought essentially to rest, without conscious effort of the user, until such time as proper placement for interproximal insertion of the floss has been made and intentional and substantial force is applied to the floss by contact with the teeth.

The invention is defined therefore in its broad sense as a powered dental flossing device comprising a power element, an oscillation unit connected thereto for actuation thereby, and a floss stringer connected to said oscillation unit, wherein said oscillation unit has a clutch mechanism for imparting oscillatory motion to said stringer essentially only when substantial force is exerted against the floss held thereby. In certain more specific aspects, the said clutch is defined as comprising a cam connected to said power element and a follower connected to said stringer, said cam and follower being normally substantially in non-contact but which are brought into substantial contact by force exerted against said stringer, said cam being adapted to impart oscillatory motion to said follower and said stringer when said cam and follower are in substantial contact and said cam is rotated by said power element.

The invention will become more understandable from the following description and drawings wherein:

FIG. 1 is a partial cross-sectional side view of the flossing device;

FIG. 2 is a partial cross-sectional view of the flossing device of FIG. 1 rotated 90°; and, FIG. 3 is an enlarged, partially cross-sectional view of the floss stringer.

Referring to the drawing, the present powered flossing device generally designated 10, comprises a power element 12 such as an electric motor or other type motor such as air or fluid operated suitably secured in a housing 14 which also serves as the handle or gripping portion of the flossing device, an oscillation unit generally designated 16 and defined further below, and a floss stringer 18.

The motor shaft 20 is provided with a drive gear 22 and provides power to the oscillation unit 16. A suitable electrical switching means (not shown) is typically mounted in housing 14 for making and breaking electrical circuit from an electrical source such as batteries contained in the housing to the motor 12 which typically turns about 1250–1750 rpm. The power unit, housing, electrical switch, and other portions of the present device which are not specifically shown in the drawing or described in detail herein may be conventional construction such as shown in U.S. Pat. Nos. 4,014,354, and 4,388,957 incorporated herein by reference.

The oscillation unit 16 comprises a ring gear 24, shaft 26, cam 28, follower 30, and rod 31. Ring gear 24 is fixed to shaft 26 which is mounted for concentric rotation in a pair of bearing plates 32 and 34 which are shown, for example, as formed integrally with or connected to the shell of motor 12. Cam 28 is formed on or affixed to shaft 26 to provide a lobe surface 36. Follower 30 is provided with a generally circular internal follower surface 38 and is formed with or connected to rod 31. Cam 28 and follower 30, having the relative dimensions described in a greater detail below, form the "clutch" which constitutes a principal aspect of the present invention. The outer ends of bearing plates 32 and 34 are formed with or affixed to a cap 40 having a rod guide in the nature of slot 42 therein for allowing essentially only up and down lateral movement of rod 31 as it reciprocates longitudinally therethrough as viewed in FIG. 1. Rod 31 is shown in FIG. 2 to have an off-set at 44 only however, for the purpose of rendering more symmetrical the particular structure shown in the drawing such that rod 31 exits the housing along the longitudinal axis thereof.

A rubber or elastomeric grommet 46 is preferably provided in the removable end 48 of the housing and provides a resilient bearing surface and fulcrum for rod 31 for developing a lateral up and down motion component therefor. Affixed to the end of rod 31 is the floss stringer 18, preferably by removable means such as socket 50 in the stringer which is frictionally but removably securable to rod 31. Suitable cooperating key-way or shoulder means may be provided on the end of rod 31 and socket 50 to insure that the stringer 18 is angularly positioned on rod 31 such that the proper oscillating motion is imparted to the floss 33. The stringer carries a pair of tines 52 and 54 curved as shown in FIG. 1 for easy access to the teeth and which are provided on their tips with floss-positioning detents 56 and along their lengths with floss guide grooves 58. Any suitable floss locking means may be provided anywhere on the flossing device for maintaining proper tension on the floss. Such means is shown as button 60 connected to or formed on the stringer in such a manner as to provide a circular wedge shaped crevice 62 lying between the underside of the button and the top of the stringer. This crevice is of such a dimension and configuration that one or more turns of the floss therearound will wedge it into the crevice and prevent it from slipping and loosening between the time tips. Unwinding the floss will of course release it from the crevice for replacement with new floss. Any such floss retaining means, as also any of the various floss dispensing means known in the art may be used, and typical of such are the devices described in U.S. Pat. Nos. 4,162,687; 4,338,957; 3,927,686; 3,534,745; 3,759,274; 3,828,804; 3,835,872; 3,960,159; and 3,472,247; all incorporated herein by reference.

In the operation of the present device, actuation of the electrical switch will actuate motor 12 to rotate drive gear 22, ring gear 24 meshed therewith and shaft 26 carring cam 28. It is noted that the surface of cam 28, especially lobe surface 36, is purposely dimensioned to provide spacing between the cam 28 and the follower surface 38. This spacing is for the purpose of allowing when desired, cam 28 to rotate without imparting oscillatory motion to follower 30, rod 31 and floss stringer 18. This clutch or lost motion feature is very desirable, as aforesaid, in allowing the floss to remain substantially at rest until sufficient force is applied thereto to move follower 30 via the resultant longitudinal and/or lateral movement of rod 31 into contact with the rotating cam 28 whereby the contact will begin the oscillatory motion of the floss. The spacing between lobe surface 36 and follower surface 38 may be varied depending on how much force one desires for making the aforesaid contact, and on the degree and character of the oscillatory motion one desires for the floss. A desirable clutching or lost-motion effect can be achieved from the overall dimensions shown in the drawing by having, for example, the difference between the major transverse dimension ("D" in FIG. 2) of cam 28 and the smallest diameter of the cavity 39 defined by the cam follower surface 38 (if this surface is not exactly circular) from about 0.003 to about 0.125 inches, preferably from about 0.006 to about 0.060 inches. Other dimensions may, of course, also be found desirable and the present invention is not limited by such, nor by the configuration of either cam 28 or surface 38.

In a preferred embodiment of the present invention cam follower 30 is normally urged by automatic spacing means such as springs 64 (either tension or compression) to its neutral position wherein no contact is made with cam 28. These springs are attached to follower 30 and a stationary portion of the device such as housing 14 by any suitable means. A light force, e.g. that equivalent to the application of 5-150 grams either laterally or longitudinally to the floss will override the spring resistance and bring follower surface 38 into contact with cam 28 to begin the oscillation of the floss. The strength (constants) of springs 64 can be determined readily by those skilled in the art to give the desired force necessary for starting the floss oscillation. The aforesaid 5-150 g. force is only representative of an operable range and can be widely varied. For example, a minmum force such as about 25 g. is desirable and as much as 200-500 g. or more of force may be required to make full contact of cam 28 with follower 30 and develop full power oscillation. It is noted that without such automatic clutch means the present device is still operable but may not give the feel at times of being in a completely neutral postion even though for preferred embodiments, it is only through the application of significant force e.g., 25 grams or more that substantial oscillatory or vibratory motion of the floss stringer and floss occurs. Such minimum force requirement for developing substantial oscillation is important for full utilization of the present invention since unintentional and usually light contact of the tines with soft tissues of the mouth will inevitably occur and at such times, significant oscillatory motion of the tines is undesirable.

In FIG. 4 is shown a variation of the automatic spacing means wherein the grommet 46 contitutes the same. In this embodiment, the rod contacting portion (bore) of the grommet is elongated and positioned on the rod by means of its annular rib 45 frictionally held in the mating annular groove 47 in the rod 31. The composition of the grommet, its physical characteristics of flexibility and the like, and its dimensions are selected such that the desired amount of force (as described above) on the floss will distort the grommet and allow cam 28 to engage follower 30. In another variation (not shown in the drawing) of the automatic spacing means, the neutral postion of the clutch is maintained by a flexible member such as a rubber strip or band attached to and stretched between bearing plates 32 and 34 and connected (contacting) to rod 31, e.g., by passng through a fairly tight aperture in rod 31 at a convenient point, e.g., about midway between slot 42 and follwr 30. Again, the stretch aand flexibility characteristics of this member are selected to give the desired resistance to the floss which must be overcome to engage the cam with the follower.

As indicated above, the shape and relative dimensions of cam 28 and follower surface 38 can be varied by those skilled in the art to impart any desirable degree and form of oscillatory motion to the floss. In the device as shown herein, the floss motion is substantially circular or elipitcal on the plane of the drawing as viewed in FIG. 1. In like manner the ratio of gears 22/24 may be varied to give any desired oscillation frequency, e.g., from about 4-100 or even up to about 1000 or more oscillations per second, with from about 7-20 per second being most preferred.

The invention has been described in detail with particular reference to preferred embodiments thereof, but it will be understood that variations and modifications can be effected within the spirit and scope of the invention.

I claim:

1. A powered dental flossing device comprising a power element having an electrical motor with an output shaft having drive means thereon, an oscillation unit having driven means engaging said drive means for actuation thereby, a floss stringer connected to said oscillation unit, said oscillation unit further having cam means connected to said driven means, cam follower means on said stringer and engageable with said cam means for actuation thereby, and said follower means being formed to provide a clutch mechanism for imparting oscillatory motion to said stringer essentially only when substantial force is exerted against the floss held thereby.

2. The device of claim 1 wherein said clutch comprises a cam connected to said power element and a follwer connected to said stringer, said cam and follower being normally substantially in non-contact but which are brought into substantial contact by force exerted against said stringer, said cam being adapted to impart oscillatory motion to said follower and said stringer when said cam and follower are in substantial contact and said cam is rotated by said power element.

3. The device of claim 2 wherein said follower has an internal follower surface defining a cavity, said cam is mounted for rotation within said cavity, and the major transverse dimension of said cam is at least about 0.006 inches less than the smallest diameter of said cavity.

4. The device of any of claims 2 and 3 wherein automatic spacing means are provided for continually urging said follower to its neutral position, said means being adapted to be overridden by force applied to dental floss mounted on said stringer.

5. The device of claim 4 wherein said force is from about 5 to about 150 grams.

6. The device of claim 4 wherein said automatic spacing means comprises at leaast two springs symetrically arranged around said follower.

7. The device of claim 4 wherein said automatic spacing means comprises three tension springs each substantially symetrically attached at their one end to said follower and at their other end to a stationary portion of said device.

8. The device of claim 4 wherein said automatic spacing means comprises a flexible member connected to a stationary portion of the device and to a rod connecting said stringer to said follower, whereby force exerted against dental floss affixed to said stringer will deform said flexible member and engage said follower with said cam.

9. The device of claim 8 wherein said flexible member comprises a grommet fixed at its periphery to a stationary portion of the device, and fixed at its bore to said rod.

10. The device of claim 8 wherein said flexible member comprises a rubber strip or band attached to and stretched between stationary portions of said device and connected to said rod.

* * * * *